United States Patent [19]

Avni et al.

[11] Patent Number: 4,966,455
[45] Date of Patent: Oct. 30, 1990

[54] REAL TIME MOTTLE MEASURING DEVICE AND METHOD

[75] Inventors: Eitan Avni, Langhorne, Pa.; Sal A. Pace, Trenton, N.J.

[73] Assignee: Union Camp Corporation, Wayne, N.J.

[21] Appl. No.: 280,166

[22] Filed: Dec. 5, 1988

[51] Int. Cl.$^5$ .................. G01N 21/47; G01N 21/57; G01J 4/00
[52] U.S. Cl. ..................... 356/73; 250/571; 356/369; 356/446
[58] Field of Search ............... 356/445, 446, 369, 429, 356/73; 250/559, 571

[56] References Cited

U.S. PATENT DOCUMENTS

| | | | |
|---|---|---|---|
| 2,755,702 | 7/1956 | Cook | 356/446 X |
| 4,213,708 | 7/1980 | Lucas | 356/446 X |
| 4,831,264 | 5/1989 | Fujiwara | 250/372 |

Primary Examiner—Vincent P. McGraw
Attorney, Agent, or Firm—Edward J. Sites

[57] ABSTRACT

Devices and methods for measuring mottle of paper-like materials are provided. the invention includes directing a radiation over a paper-like material and scanning it in a plurality of directions. Radiation scattered by the paper-like material is detected to produce an output. This output is processed to provide a reading proportional to the mottle of the paper-like material. The invention uses electro-optical devices and signal processing to quantify mottle as an appearance property. Gloss measurements of the paper-like material can also be quantified and simultaneously displayed.

17 Claims, 6 Drawing Sheets

FIG. 2a — COARSE MOTTLE

FIG. 2b — MEDIUM MOTTLE

FIG. 2c — MEDIUM-FINE MOTTLE

FIG. 2d — FINE MOTTLE

FIG. 2e — UNMOTTLED

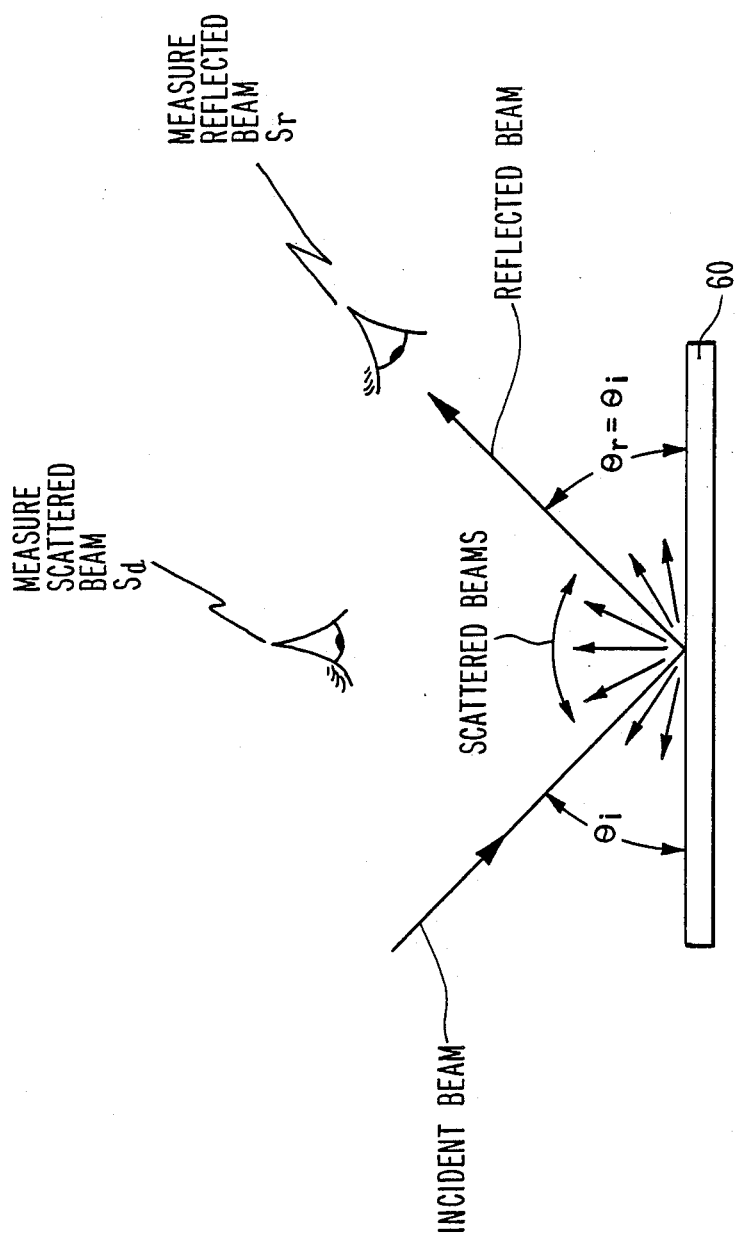

REAL TIME MOTTLE MEASURING DEVICE AND METHOD

FIELD OF THE INVENTION

This invention relates to devices and methods for measuring surface properties of paper-like materials, and particularly to devices for the measurement of mottle and surface gloss of paper in real-time manufacturing environments.

BACKGROUND OF THE INVENTION

Mottle can be generally defined as the irregularities in the visual appearance of a sheet of paper or paper-like material. The irregularities can be caused by variations in the color, color intensity, or relative amount of gloss. Mottled appearance is also caused by variations in the coatings applied to the surface of the paper. Certain types of coated paper, such as paper having a coating of filled polyethylene etc., often have a mottled appearance if there is a "show through" of the underlying irregularities through the coating. Such surfaces may still exhibit high gloss and a smooth texture. A similar, but slightly different, variation of mottle is obtained when a white blocking coating is applied over the surface of a paper.

Currently, the degree of mottle is determined by highly subjective, visual inspection. Subjective ratings of mottle can vary widely between operators and between customers and their manufacturers. There has been a long felt need in the paper industry to obtain an objective standard by which to measure mottle which is related directly to the established subjective standards. There has also been a long felt need to evaluate the degree of mottle on a consistent objective basis.

Various prior methods have been employed to determine the surface properties of paper and other materials. Some have included radiation sources and collectors capable of receiving a portion of the radiation being reflected from a sheet of material and detectors capable of measuring select properties of the sheet based upon the radiation received. See U.S. Pat. Nos. 4,277,177, 4,319,847. Others have employed elaborate lens systems or multiple photodetectors for determining roughness or surface defects. See U.S. Pat. Nos. 4,364,663 and 4,465,371. Additionally, the use of tuned amplifiers and Fourier transform spectrums which rely on the differentiation in diffraction patterns have been employed for increasing the sensitivity of detection of flaws in a surface. See U.S. Pat. Nos. 4,465,371 and 4,338,822. Despite these teachings, however, the paper-making art has not generated a suitable apparatus for making an objective determination of mottle.

SUMMARY OF THE INVENTION

Novel mottle measuring devices and methods are provided by this invention which include a radiation source projected at the surface of a paper-like material. The radiation from this source is scanned in a plurality of directions to present a mottle reading representative of the entire area of the sample. The invention further includes a detector for selectively receiving at least the radiation associated with scattering by the paper-like material. The detector provides an output representative of a detected scattered radiation which is then inputted into a processing apparatus for providing a reading which is proportional to the mottle of the paper-like material.

Accordingly, the present invention teaches a method and apparatus for measuring mottle and/or degrees of mottle so as to obtain an objective reading which can be correlated with the subjective readings obtained by examination with the human eye. The invention satisfies a long-felt need in the paper making industry for providing consistent, real-time mottle measurements.

In further embodiments of this invention, a light source, such as a laser beam or the like, is directed at the surface of a paper at a predetermined angle. Reflected light is ignored and the scattered light is measured by a photodetector or other means for determining variations in the amount of scattered light. The invention includes scanning the light over a representative area of the sheet of paper to obtain an overall evaluation of the pattern of mottle. This is clearly an advantage over prior art techniques for measuring in only a machine direction, which may yield results that are not representative of the overall mottle appearance. The invention further includes a filter for screening out transient signals due to holes or dirt particles, etc. Noise is minimized by digital signal processing and a Fourier transform process is employed to determine the periodicity of the mottle. The methods and devices provide a indication which can be related to the subjective appearance of the mottle. Thus, a relatively objective evaluation of mottle can be provided to those in the art to satisfy the long felt need for consistency in mottle determinations.

It is, therefore, an object of this invention to provide a real time mottle measuring device and method which obtain an overall mottle reading representative of the entire paper sample.

It is another object of this invention to provide means for separating noise and transient information to provide a more accurate reading of mottle.

It is still another object of this invention to provide a correlation between subjective evaluations of mottle and the objective evaluation obtained by real-time measuring devices.

With these and other objects in view, which will become apparent to one skilled in the art as the description proceeds, this invention resides in the novel construction, combination, arrangement of parts, and methods substantially as hereinafter described and more particularly defined by the attached claims.

BRIEF DESCRIPTION OF THE DRAWINGS

The accompanying drawings illustrate preferred embodiments of the invention according the practical application of the principles thereof, and in which:

FIG. 9: is a diagrammatical illustration of the separation techniques used to determine beam scattering and reflectivity.

DESCRIPTION OF THE INVENTION

The operable embodiments of this invention will now be described. One preferred device includes a radiation source means for directing a radiation on a paper-like material and a scanning means for scanning the radiation source means in a plurality of directions. The device further includes detector means for detecting at least a radiation scattered by the paper-like material and for providing an output representative of a detected amount of scattered radiation. Finally, the device comprises processing means for receiving the output from the detector means and for providing a reading proportional to the mottle of the paper-like material.

In another preferred embodiment of this invention, a device for measuring mottle is provided which includes a light source for directing a polarized light at a predetermined angle on a paper-like material. This embodiment further includes scanning apparatus for scanning the polarized light in a plurality of directions on the paper-like material. First detector means are included for detecting at least a light scattered by the paper-like material and for providing an output representative of a detected amount of scattered light. Second detector means are provided for detecting at least a polarized light reflected by the paper-like material and for providing an output representative of a detected amount of reflected, polarized light. The second detector means is disposed at the same preselected angle for receiving the reflected polarized light. This embodiment further includes processing means for receiving the output of the first and second detector means and for providing readings proportional to the mottle and gloss of the paper-like material.

In the context of this invention, the term "paper-like material" refers to any substantially planar material, preferably cellulosic, thermoplastic, or combinations of cellulosic and thermoplastic materials. The term "mottle" refers to changes in the overall appearance of the paper-like material due to reflected light from the surface, and is not meant to refer to transmitted light due to variations in the formation of the paper-like material.

In the preferred method of this invention, a radiation is directed to a paper-like material. The radiation is scanned in a plurality of directions and then the scattered portion of this radiation is detected and an output proportional to the detected amount of scattered radiation is provided. This output is then processed to provide a reading proportional to the mottle of the paper-like material.

Figure 1:
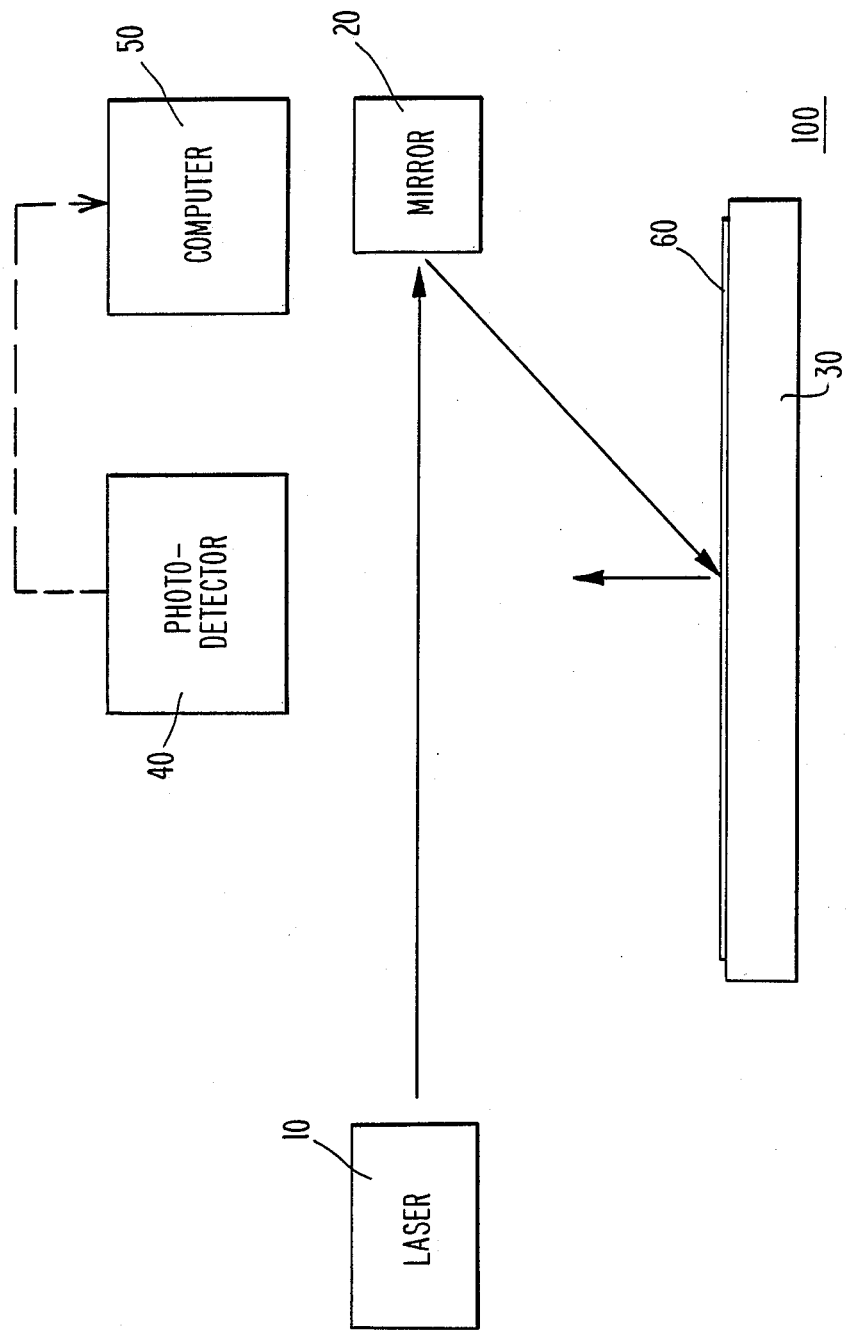
FIG. 1: is a diagrammatic representation of a preferred mottle measuring device of this invention.

Referring now to the figures, and particularly to FIG. 1, a novel device 100 for measuring mottle of a paper-like material is provided. A light source, preferably a laser 10, is projected directly at the surface of the paper, or reflected from a mirror 20 and then directed to the paper-like material 60. In a preferred embodiment, the reflected light is ignored and scattered light is measured with photodiode 40, or similar device. The photodiode 40, picks up the scattered light and converts the light into a corresponding analog electrical signal, which is then processed to determine the relative degree of mottle by the processing means, or preferably an IBM XT ® 50.

In the more preferred embodiments, a light source, such as the laser beam 10, or the like is directed at the surface of the paper-like material 60 at a predetermined angle, such that the reflected light can be ignored. The intensity of the scattered light can be measured with a photodetector 40 to pick the variations in the amount of scattered light. In order to obtain meaningful data, the light should be projected over a representative area of the sheet of paper to obtain an overall evaluation of the pattern of mottle.

In an important aspect of this device 100, scanning means are provided, such as movable stage 30, for directing the radiation source in a plurality of directions on the paper-like material. It is expected that either the light source, mirror 20, or movable stage, can be put into motion to provide means for scanning. Although conventional scanning, such as by providing a fixed beam on a paper at a fixed point and allowing the paper to travel, will provide meaningful data, it is not preferred. Such information would give a machine direction mottle for a particular portion of the width of the sheet which may not be representative of the overall mottle appearance. Preferably, the beam of light is raster scanned, preferably with a raster scan and/or flyback between scans coupled with a possible calibration scan of a known surface, such as an edge of a roller, or the like, in order to obtain overall mottle readings representative of the entire area of the paper sample.

The detector means, preferably including photodiode 40, produces an output representative of a detected amount of scattered radiation in the preferred embodiment. The light signal picked up by the photodiode 40 is initially converted into an electrical signal. This signal would generally be an analog signal and would show a great deal of diversion with regard to the signal elements of the analog reading. Although this signal could be used as a subjective evaluation of the mottle, it is considered no more valuable than subjective eye examinations. Accordingly, an objective evaluation is preferably made of the relative appearance of the resulting recorded signal in order to obtain a correlation between the reading and the paper. This is accomplished by processing the data according to the following description.

The processing sequence of this invention includes various steps which can be used either individually or in combination to process the signal. Preferably, the initial processing of the signal includes use of filter means for removing transient signals, e.g. those associated with holes, foreign matter and dirt particles on the paper-like material. A signal associated with the light source can be separated from noise signals using ammodulation/demodulation techniques, tuning devices, and/or band pass filters known to those of ordinary skill in the art. Preferably the analog signal is digitized in order to reduce some of the divergences from a base line within a given signal. The signal versus location on the sheet is transferred to a preferred microprocessor which includes preferred calculating means such as Statgraphic Software ®.

In the most preferred processing means, reflectivity variance is determined over the surface link of measurement. Fourier transformation of the reflectance signal, or pattern recognition could also favorably be employed. The quantitative measurements are then usable in place of subjective quality indications. For example, surface mottle in printed and unprinted papers can be characterized by varying degrees of reflectivity fluctuation across the sheet surface with characteristic frequencies identifiable through Fourier techniques. Accordingly, the device and method can determine a mottle value relative to a subjective appearance of the mottle in the paper-like material.

The additional signal can be processed through a suitable personal computer employing Fast Fourier Transform ® (FFT) software. The computer conducts calculations on the signal in order to determine the periodicity of the mottle, and determine a frequency of a predetermined degree of change in the signal relative to the degree of mottle in the paper. Once the periodicity of the pattern is determined, it can be converted into a number which would be relative to the subjective appearance of the mottle. The frequency and the value for a mottle can then be converted into an objective reading to thereby present the relative amount of mottle objectively.

Figure 2:
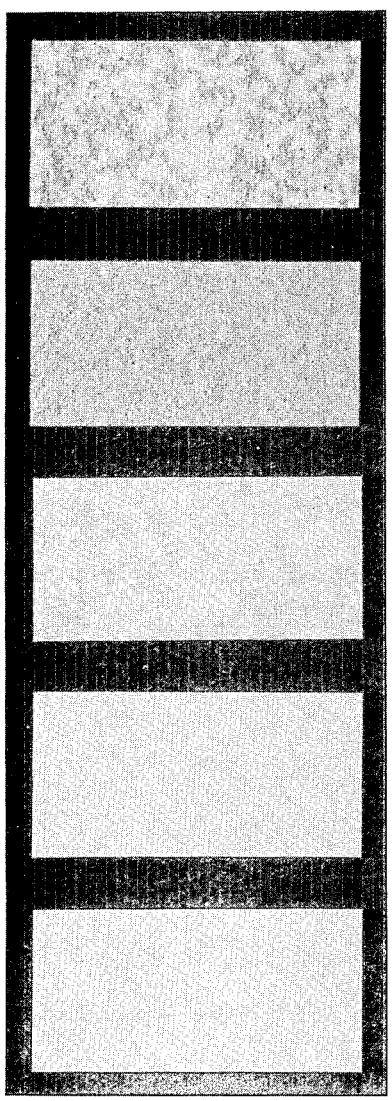
FIG. 2(a)–(e): are representative illustrations of the general appearances of course mottle, medium mottle, medium-fine mottle, fine mottle and unmottled as used in this invention.
Figure 3:
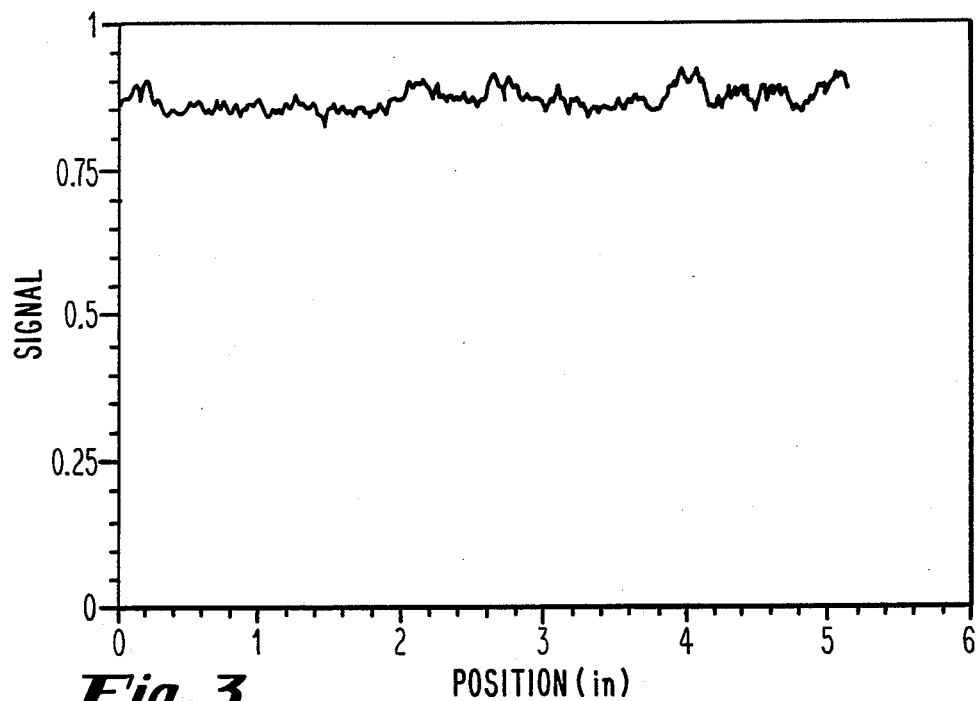
FIG. 3: is a graph depicting an actual scan readout in a machine direction of fine mottle sheet illustrating the signal versus the paper position in inches.
Figure 4:
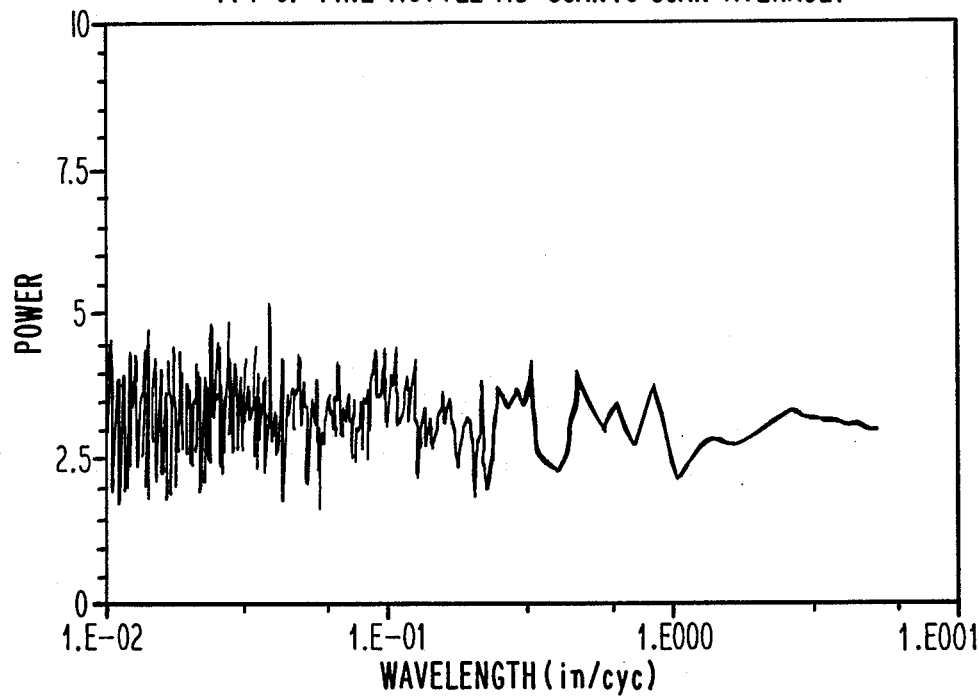
FIG. 4: is a graphical depiction of a Fast Fourier Transform ® (FFT) of fine mottle scanned in a machine direction illustrating power versus wave length in inches per cycle.
Figure 5:
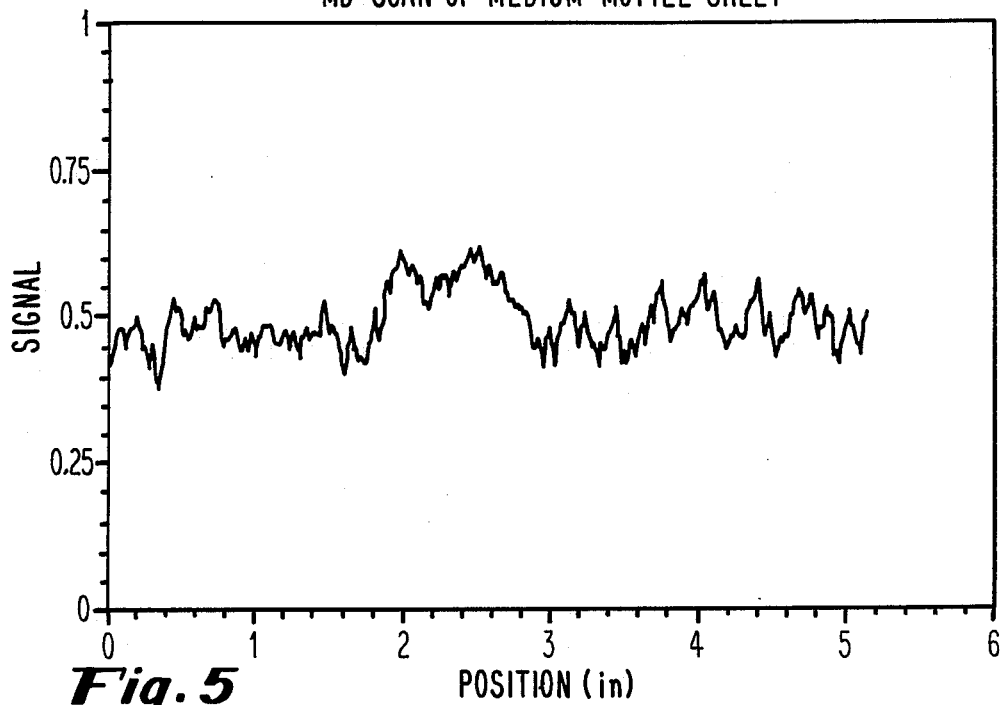
FIG. 5: is graph depicting an actual scan readout in a machine direction of medium mottle sheet illustrating the signal versus the paper position in inches.
Figure 6:
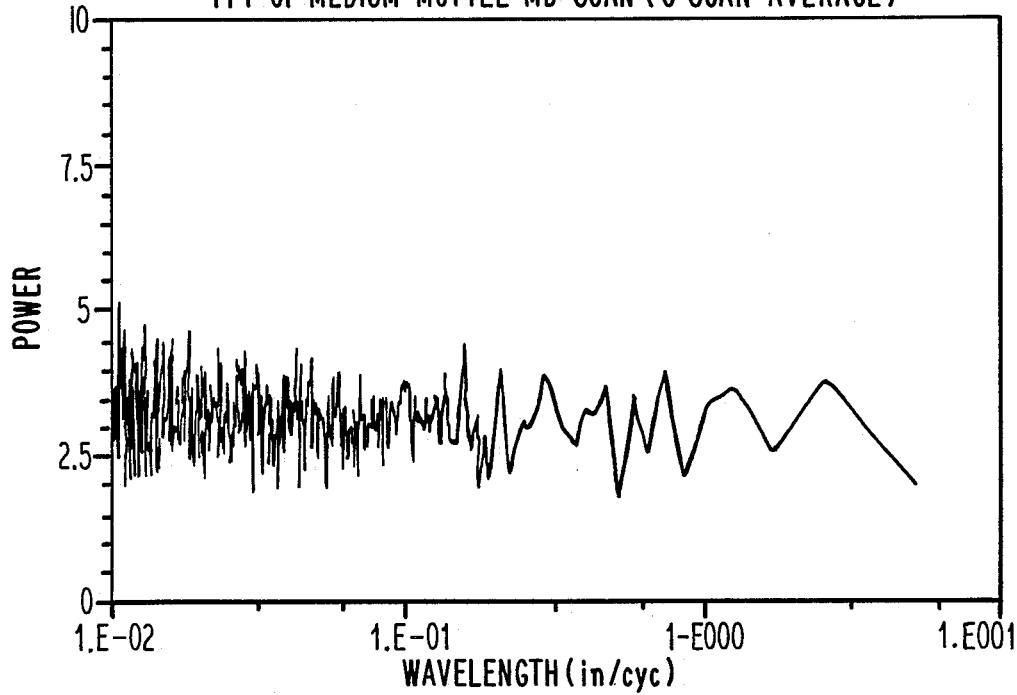
FIG. 6: is a graphical depiction of a Fast Fourier Transform ® (FFT) of medium mottle scanned in a machine direction illustrating power versus wavelength in inches per cycle.
Figure 7:
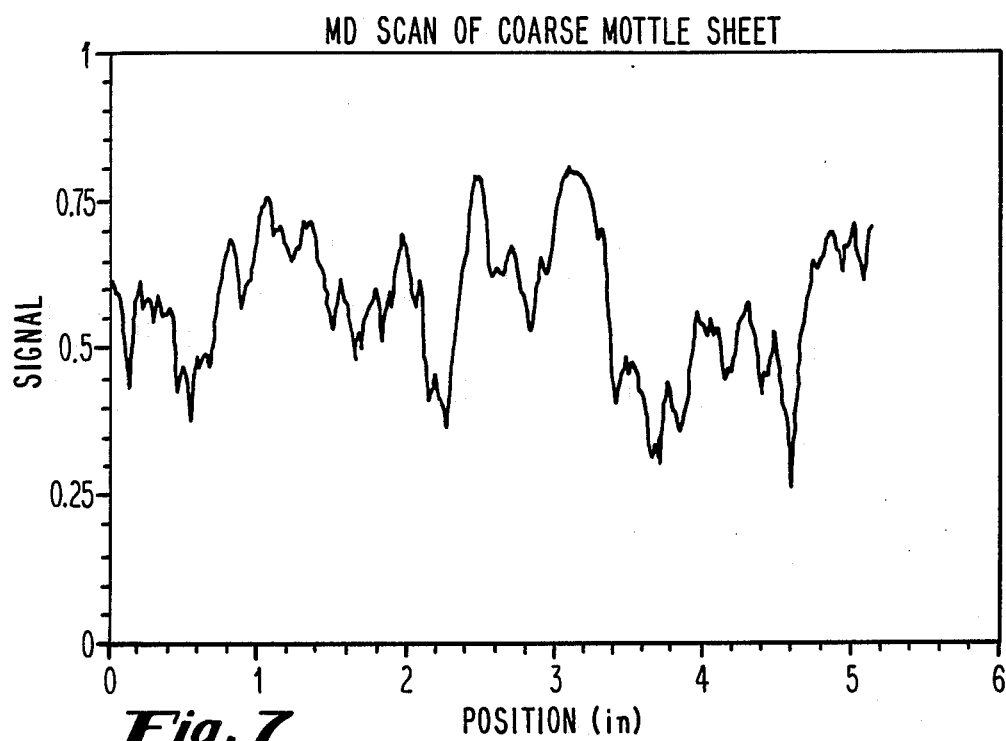
FIG. 7: is a graph depicting an actual scan readout in a machine direction of coarse mottle sheet illustrating the signal versus the paper position in inches.
Figure 8:
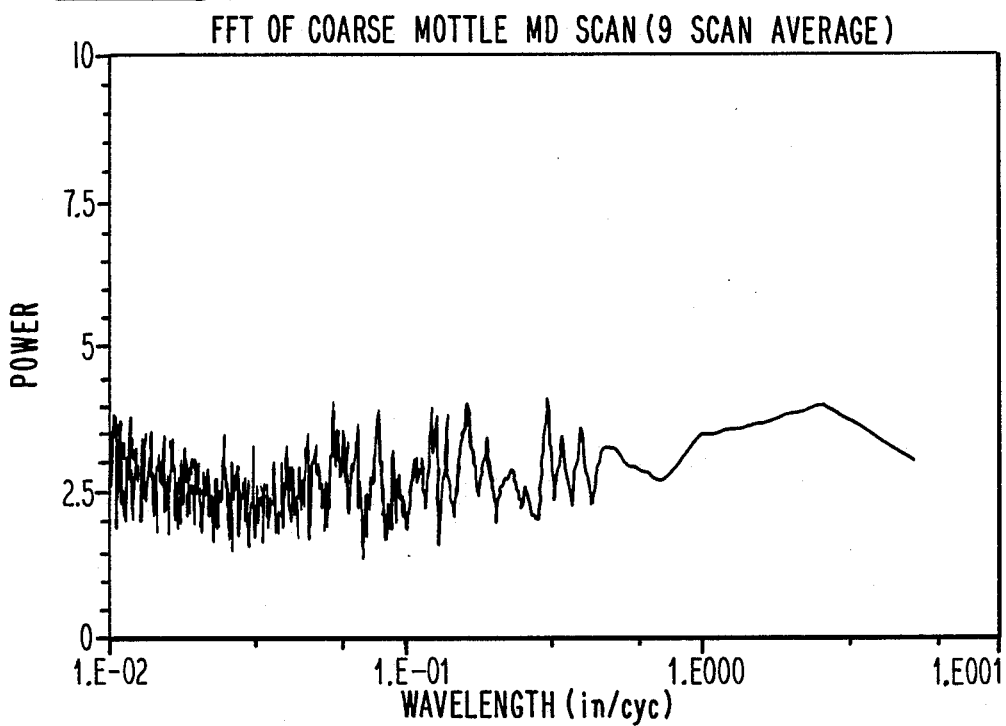
FIG. 8: is a graphical depiction of a Fast Fourier Transform ® (FFT) of coarse mottle scanned in a machine direction illustrating power versus wavelength in inches per cycle.

Referring now to the mottle descriptions of FIG. 2(a-c), three degrees of mottle are described, namely, fine mottle, medium mottle, and coarse mottle. The actual scans for these mottle samples are described in FIGS. 3, 5, and 7. Their corresponding FFT analysis plots are shown in FIGS. 4, 6, and 8 respectively. The actual scans appear to correlate well with their respective samples. As described by the scans, the variation in signal amplitude greatly increases from the fine mottle sheet to the coarse mottle sheet, which is indicative of the incidence of light and dark variations in the sheets themselves.

In the alternative embodiment FIG. 9, a dual detector system is described for separating reflectivity and scattering signals. This permits simultaneous measurement of gloss and smoothness. The concept is to measure the total reflected beam and subtract it from the beam due to scattering to obtain the true reflected beam. The reflected beam is related to gloss and the scattered beam is related to mottle.

This simplified concept is described by the following formula:

(1) $S_d(0)$ = constant a all angles
(2) $S_{Total}(0_r) = S_d(0_r) + S_r(0_r)$
(3) $S_r = S_{Total}(0_r) - S_d$
(4) $S_d$ roughness
(5) $S_r$ gloss where:
$S_r$ = reflected light beam measure
$S_d$ = diffused beam scattering measure
$S_{Total} = S_d + S_r$
$0$ = angle
$0_i$ = incident beam angle
$0_r$ = reflected beam angle
$S_{Total}(0_r)$ = total beam at $0_r$
$S_d(0_r)$ = scattered beam at $0_r$
$S_d(0)$ = scattered beam at all angles In an alternative embodiment of this invention illustrate in FIG. 9, polarized light could be employed as the incident beam. The reflected beam would still be polarized, while the scattered beam, also referred to as the diffuse beam, would not. By detecting the beam at a predetermined reflectance angle, one can quantify the degree of retention of polarization. The fraction of polarized light in the reflected beam would be a measure of true gloss. In this embodiment, the device could be used for on-line monitoring of mottle and gloss individually or simultaneously.

From the foregoing it can be realized that this invention provides an improved device and method for measuring mottle and/or gloss of a paper-like material in real-time. The invention quantifies mottle as an appearance property by using electro-optic devices and signal processing. The invention has tremendous potential as an on-line production device or bench-top lab apparatus. Although mechanical elements and process steps have been illustrated, this was for the purpose of describing, but not limiting, the invention. Various modifications, which will become apparent to one skilled in the art, are within the scope of this invention described in the attached claims.

We claim as our invention:

1. A device for measuring mottle of a paper-like material, comprising:
   (a) radiation source means for directing a radiation on said paper-like material, said radiation source means comprising light source means having polarization means for producing a light on said paper-like material at a specified reflection angle;
   (b) scanning means for scanning said radiation in a plurality of directions on said paper-like material;
   (c) detector means for detecting at least a radiation scattered by said paper-like material and for providing an output representative of a detected amount of scattered radiation;
   (d) processing means for receiving said output of said detector means and for providing a reading proportional to the mottle of the paper-like material.

2. The device of claim 1 wherein said scanning means comprises a raster scanner.

3. The device of claim 2 wherein said scanning means further comprises a flyback apparatus.

4. A device of claim 3 wherein said scanning means further comprises a calibration scanner.

5. The device of claim 1 further comprising filter means for removing transient signals.

6. The device of claim 5 wherein said filter means comprises means for removing signals caused by holes and foreign matter.

7. The device of claim 1 wherein said processing means comprises signal processing means for digitizing said output of said detector means and for removing noise.

8. The device of claim 1 wherein said processing means comprises calculation means for determining a periodicity of the mottle in said paper-like material.

9. The device of claim 8 wherein said calculating means comprises Fourier transform means.

10. The device of claim 1 wherein said processing means further comprises means for determining a value relative to a subjective appearance of the mottle in said paper-like material.

11. The device of claim 1 wherein said processing means comprises means for quantifying a degree of retention of polarization.

12. The device of claim 11 wherein said processing means further comprises means for providing a reading proportional to the surface gloss of said paper-like material.

13. A method of determining a measurement of mottle of a paper-like material, comprising:
(a) directing a polarized light on said paper-like material at a specified reflection angle;
(b) scanning both a scattered and a reflective light in a plurality of directions on said paper-like material;
(c) detecting at least said scattered light and providing an output proportional to a detected amount of scattered light;
(d) processing said output to provide a reading proportional to the mottle of the paper-like material.

14. The method of claim 13 wherein said processing step (d) further comprises filtering transient signals.

15. The method of claim 14 further comprising signal processing said output to produce a signal representative of reflected light.

16. The method of claim 14 further comprising signal processing said output to provide a signal representative of scattered light.

17. A device for measuring mottle of a paper-like material, comprising:
(a) a light source for directing a polarized light at a predetermined angle on a paper-like material;
(b) scanning apparatus for scanning said polarized light in a plurality of directions on said paper-like material;
(c) first detector means for detecting at least a light scattered by said paper-like material and for providing an output representative of a detected amount of scattered light;
(d) second detector means for detecting at least a polarized light reflected by said paper-like material and for providing an output representative of a detected amount of reflected, polarized light, said second detector means disposed at said preselected angle for receiving a reflected polarized light; and
(e) processing means for receiving said output of said first and second detector means and for providing readings proportional to the mottle and gloss of the paper-like material.

* * * * *